United States Patent [19]

Pollack et al.

[11] Patent Number: 5,014,699

[45] Date of Patent: * May 14, 1991

[54] ELECTROMAGNETIC METHOD AND APPARATUS FOR HEALING LIVING TISSUE

[75] Inventors: Solomon R. Pollack, Dresher; Carl T. Brighton, Malvern; David Pienkowski, Exton, all of Pa.; Neil J. Griffith, San Diego, Calif.

[73] Assignee: Trustees of the University of Pennsylvania, Philadelphia, Pa.

[*] Notice: The portion of the term of this patent subsequent to Mar. 12, 2008 has been disclaimed.

[21] Appl. No.: 443,741

[22] Filed: Nov. 30, 1989

Related U.S. Application Data

[63] Continuation-in-part of Ser. No. 313,332, Feb. 21, 1989, which is a continuation of Ser. No. 866,877, May 23, 1986, abandoned, and a continuation-in-part of Ser. No. 88,711, Aug. 24, 1987, abandoned, and a continuation-in-part of Ser. No. 192,012, May 9, 1988, abandoned.

[51] Int. Cl.$^5$ ............................................. A61N 1/00
[52] U.S. Cl. ................................... 128/419 F; 600/9; 600/13; 600/14
[58] Field of Search ................... 128/419 F, 422, 423; 600/9, 10, 11, 12, 13, 14

[56] References Cited

U.S. PATENT DOCUMENTS

| | | | |
|---|---|---|---|
| 4,266,532 | 5/1981 | Ryaby et al. | 128/419 F |
| 4,574,809 | 3/1986 | Talish et al. | 128/419 F |
| 4,616,629 | 10/1986 | Moore | 128/419 F |
| 4,620,543 | 11/1986 | Heppenstall et al. | 128/419 F |
| 4,641,633 | 2/1987 | Delgado | 600/13 |
| 4,674,482 | 6/1987 | Waltonen et al. | 128/419 F |

*Primary Examiner*—Francis Jaworski
*Assistant Examiner*—George Manuel
*Attorney, Agent, or Firm*—Woodcock Washburn Kurtz Mackiewicz & Norris

[57] ABSTRACT

A non-invasive, portable electromagnetic therapeutic method and apparatus for promoting the healing of damaged or diseased living tissue including fractured bone and in particular nonunion or delayed union bone fractures are described. The method and apparatus involve generating a signal having a series of substantially symmetric voltage cycles of bursted pulses having narrow pulse widths on the order of 0.5 to 20 microseconds and converting the signal into an electromagnetic field which extends into an area for desired tissue healing. The portable noninvasive apparatus can be readily worn or carried by a patient and is capable of generating an energy-efficient symmetrical signal coacting with a coil for transducing the signal into electromagnetic pulses.

81 Claims, 6 Drawing Sheets

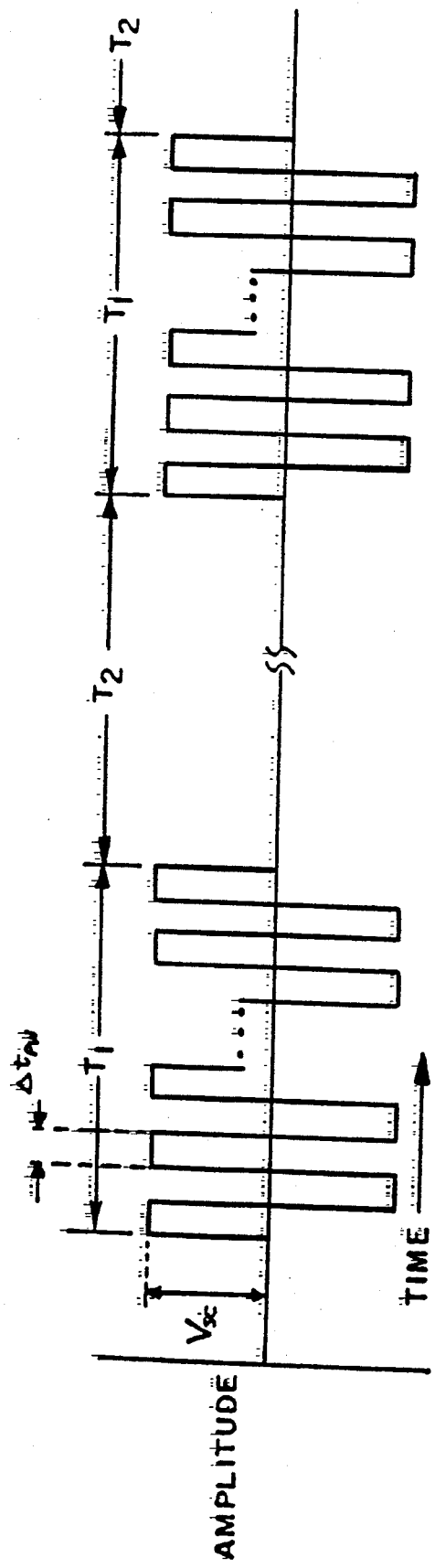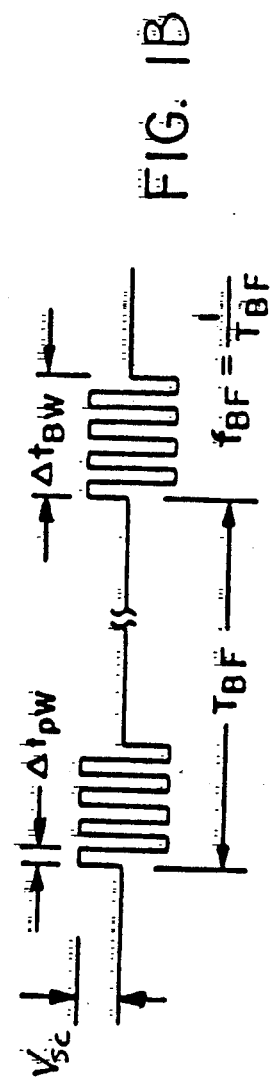
FIG. IA
FIG. IB

| COIL TYPE: | SIMPLE | OBLIQUE | SOLENOID | HELMHOLTZ |
|---|---|---|---|---|
| LIMB DIAMETER | $S$ | $S$ | $S$ | $S$ |
| $L(H)$ | $\dfrac{\pi S N^2 \times 10^{-7}}{2 \times 9.8}$ | $\dfrac{\pi \sqrt{3/2}\, S N^2 \times 10^{-7}}{2 \times 9.8}$ | $\dfrac{6 \pi S N^2 \times 10^{-7}}{2\sqrt{2} \times 9.8}$ | $\dfrac{\pi S N^2 \times 1.1 \times 10^{-7}}{2\sqrt{2} \times 9.8}$ |
| $f_c \left(\dfrac{\text{GAUSS}}{\text{AMP}}\right)$ | $\dfrac{2\pi N}{5S}$ | $\dfrac{2\pi N}{5S\sqrt{3/2}}$ | $\dfrac{\pi N \sqrt{2}}{5S}$ | $\dfrac{\pi N \sqrt{2}}{5S\sqrt{3/2}}$ |
| $K_c$ | $1.02 \times 10^{-8} S^3$ | $1.87 \times 10^{-8} S^3$ | $0.861 \times 10^{-8} S^3$ | $5.33 \times 10^{-8} S^3$ |
| NORMALIZED | 1.18 | 2.17 | 1.0 | 6.19 |

FIG. 3

ELECTROMAGNETIC METHOD AND APPARATUS FOR HEALING LIVING TISSUE

CROSS-REFERENCES TO RELATED APPLICATIONS

This application is a continuation-in-part of
1. application Ser. No. 07/313,332, filed Feb. 21, 1989, which, in turn, is a continuation of application Ser. No. 06/866,877, filed May 23, 1986, now abandoned;
2. application Ser. No. 07/088,711, filed Aug. 24, 1987 now abandoned; and
3. application Ser. No. 07/192,012, filed May 9, 1988 now abandoned.

BACKGROUND OF THE INVENTION

1. Field of the Invention

The present invention relates generally to electromagnetic methods of and an apparatus for stimulating healing of living tissue and more specifically to a method and apparatus for electromagnetic therapy to promote healing of tissue, e.g., electromagnetically stimulating osteogenesis, i.e., bone growth.

2. Discussion of the Prior Art

The process of healing diseased or damaged tissue including bone involves a variety of biochemical, cellular and tissue events, including changes in nuclear material (DNA), protein synthesis, membrane transport, progenitor-mesenchymal cell differentiation and migration, mitosis, etc.

It has long been recognized that properly applied electro-therapy signals can stimulate bone growth in the vicinity of fresh fractures and non-union fractures, and apparently do so by initiating or stimulating the requisite biochemical changes. That is, it has been thought that the stimulation of these cellular growth processes is related to the changing electrical and/or electro chemical environment of the cells present in bone. This electrical change, in turn, causes an alteration in cell behavior resulting in the synthesis of molecules produced by these cells necessary to effect bone healing. The mechanism underlying these events is thought to be an alteration of the interaction of charged species at the cell surface caused by the electrical signal. Because of the uncertainty regarding the most effective modality of electro-therapeutic treatment, including the nature of the electrical signal, and methods for applying the signal to the site of treatment, a substantial amount of research has been undertaken over quite a number of years to determine the most effective parameters.

Extensive research has been conducted in both experimental animal studies and human clinical trials utilizing various specific waveform formats for such treatment, including invasively-coupled, direct-current devices; capacitively-coupled, symmetric and asymmetric waveforms, and electro-magnetically coupled asymmetric waveforms.

There is a substantial body of prior art detailing the materials and methods used to effect electrotherapeutic bone healing, and many of these are described in the *Annals of the New York Academy of Sciences*, Vol. 238, October 1974, in an article entitled "Electrically Mediated Growth Mechanisms in Living Systems" (Editors, A. R. Liboff and R. A. Rinaldi). Excellent technical reviews of this field are J. A. Spadaro's "Bioelectric Stimulations of Bone Formation: Methods, Models and Mechanisms," in the *Journal of Bioelectricity*, Volume 1 (1), p. 99, 1982; and the *Orthopedic Clinics of North America Symposium on Electrically Induced Osteogenesis*, W. B. Saunders Corp. 1984. These reports detail variations in waveform formats for semi-invasive direct current devices, capacitively-coupled symmetric and asymmetric waveforms and inductively-coupled asymmetric waveforms.

All currently used electro-therapy techniques have one or more limitations. For example, invasive or semi-invasive techniques require at least one electrode to be inserted through the patient's skin in the vicinity of the fracture site. As with any surgical technique this will increase the risk of infection and may limit patient mobility and require subsequent operative procedures. The capacitively-coupled systems operate with a low impedance electrical connection but require that the capacitive plates be located adjacent the skin and require that they be gel-coated daily. Obviously this requires consistent patient compliance to be effective and can be annoying to the patient. The electromagnetic inductively-coupled methods and apparatuses require high power consumption waveform generation devices and bulky coil configurations which also limit the mobility of a patient to function normally outside the clinical environment.

The uncertainty regarding the most effective electro-therapeutic parameters that affect treatment is reflected in numerous patents. For instance, U.S. Pat. No. 4,467,808 (Brighton and Pollack) utilizes a 20–100 KHz signal generated by an alternating current power supply for the treatment of osteoporosis in bone. Unidirectional low voltage pulses are provided to the injury site in a non-invasive method described in U.S. Pat. Nos. 4,266,532 (Ryaby) and 4,461,663 (Delgado). A non-invasive capacitively coupled signal is disclosed in U.S. Pat. No. 4,535,775 (Brighton and Pollack). Other patents pertinent to the electro-therapy area are U.S. Pat. Nos. 3,890,953 (Kraus and Viehbach), 3,893,462 (Manning), 3,952,751 (Yanger) and 4,667,809 (Brighton).

Although the above references are primarily directed towards bone growth stimulation, there are also benefits with respect to the electromagnetic stimulation of soft tissues. These benefits are discussed in Black, "Electrical Stimulation of Hard and Soft Tissues in Animal Models," *Clinics in Plastic Surgery*, 12 (April, 1985) and Frank et al "A Review of Electro-magnetically Enhanced Soft Tissue Healing," *IEEE Eng. in Medicine and Biol*, (Dec., 1983).

It may be explained here that it generally takes bone fractures, particularly non-union fractures, many weeks or months to heal, and this is true even with the aid of electro-therapy where it has been tried as an adjunct treatment in an experimental setting. Because the presently utilized electro-therapy devices are, with a few exceptions, not truly portable, if the patient is to benefit from electro-therapy, he must have ready access to a source of electric power to effect treatment. Considering the time required for a bone to heal, this constraint is particularly annoying on a day to day basis, and requires that a patient constantly interrupt his daily routine for treatment, which may in turn cause failure of the patient to comply with the required protocol. Also, in most non-union fracture cases it is desirable for the patient to bear weight on the fracture site while maintaining the electromagnetic stimulation. A non-portable device requires the patient to remain limited in movement to the vicinity of the electromagnetic stimulator device.

Therefore, it is apparent that it is desirable to produce a device having the effective features of the devices currently in use but lacking their undesirable features, particularly their power wasting aspects. By creating a more power-efficient electro-therapy device it is possible to considerably reduce the size of the electro-therapy machines, hence permitting the construction of a completely portable device that allows the user to go about his daily routine without being tethered to a source of electric power.

A few inventors have appreciated the practical advantages of having a portable electro-therapy device. It is important to note that portability in the art is taken to mean a device readily carried by the patient without cumbersome support aids, and particularly connotes devices less than two pounds in weight, preferably less than one pound, and no larger than a small pocket camera inasmuch as portable is a relative term. U.S. Pat. No. 4,432,361 (Christensen and Mizoguchi) describes a portable device that has self monitoring features thereby allowing the patient to ascertain its operational status without having to have it checked by a physician, or another person skilled in the use of the device. This invention is an improvement over that described in U.S. Pat. No. 3,842,841 (Brighton and Freidenberg) which does not have the desirable self-monitoring features. Another portable electrotherapy device is described in U.S. Pat. No. 4,574,809 (Talish et al). It shows a device suitable for integration into an orthopedic cast with a signal generator removably mounted in the cast.

It is evident from the foregoing that there is a need for an effective electrotherapeutic method that is not limited by the currently used devices, but rather which employs a truly portable device.

SUMMARY OF THE INVENTION

In accordance with the present invention, a portable electro-therapy device having considerable advantages over prior devices is provided. In an exemplary embodiment of the invention, the deficiencies of prior art systems are overcome in a system in which an effective treatment signal is produced in a low power consumption device, and then efficiently coupled to the treatment site by transducers that may be conformed to the external body line contours in the vicinity of the treatment site so that the entire system lends itself to portable, ambulatory use. Prior to the applicants' invention, it was generally assumed that the body did not respond to short duration symmetric electromagnetic pulses, resulting in the development of bulky circuit devices for generating the long-duration pulses thought necessary for effective treatment. Applicants' have discovered an hithertofore unrecognized feature of the biology of healing realized by electro-therapy, particularly bone healing, but the effectiveness of the device encompasses healing of damaged tissues generally. The "effective treatment signal" of this invention comprises symmetrically shaped pulses, especially those of a relatively short pulse width, and especially grouped into a burst of pulses followed by a quiet time, which are as efficacious as devices applying other electrical parameters. This realization has permitted the design of a device using several orders of magnitude less power than required by existing devices. This finding, coupled with conformal transducer designs for delivering the low power signal at the damaged tissue site, permits the development of a truly portable electro-therapy device.

A variety of transducers of specific designs can contribute to the overall energy efficiency of the subject device. However, in an exemplary embodiment of the invention, the conformal assembly complex comprises a solenoidal coil of varying turns applied around a limb and connected to a power source to generate signals at the treatment site.

As applied to healing of bone fractures, the application of the invention described herein in no way affects or interferes with present treatment protocols. Thus, the physician is given a treatment option especially for those fractures, for example, nonunion fractures, which, by experience and analysis, have been determined to be most likely to require surgery or other invasive procedures.

It is an object of the present invention to provide an effective electromagnetic/therapeutic method and apparatus for efficiently stimulating tissue growth including osteogenesis.

It is a further object of the present invention to provide a method and apparatus for electromagnetic therapeutic bone growth stimulating which is non-limiting with respect to the mobility of a patient.

The above and other objects are achieved in accordance with one aspect of the present invention by the method of electromagnetic therapeutic treatment comprising the steps of:

converting an electrical potential into a series of substantially symmetric voltage cycles, each voltage cycle comprising a train of bursted pulses, each pulse having a pulse width of 0.5-20 microseconds; and transducing said voltage cycles into an electromagnetic field in the vicinity of desired tissue stimulation.

In another aspect, the present invention comprises an apparatus for electromagnetic therapeutic treatment of living tissues comprising:

means for converting an electrical potential into a series of substantially symmetric voltage cycles, each voltage cycle comprising a train of bursted pulses, each pulse having a pulse width of 0.5-20 microseconds; and transducer means for transducing said voltage cycles into an electromagnetic field in the vicinity of said damaged tissue.

In preferred embodiments of the above method and apparatus, the train of bursted pulses has a pulse in the range of about 2-10 microseconds. The use of a symmetric signal, preferably a square wave, may allow for a 50% increase in the stiffness of fractures at the mid phase of healing, promoting earlier patient mobility. Fracture stiffness is one indicator of the level of healing in a fractured bone. Applicants have found that the use of symmetrically shaped pulses, when grouped into a burst of pulses (with relatively short pulse widths) followed by a quiescent period are as effective in stimulating bone growth as are various prior art devices utilizing long duration asymmetric pulses requiring high power consumption. In the present invention the pulse width can be shortened to as low as 0.5 microseconds in order to reduce the input power requirement without reducing the bone growth stimulation effectiveness. This permits a truly portable electromagnetic therapeutic device.

BRIEF DESCRIPTION OF THE DRAWINGS

A more complete appreciation of the invention, and many of the attendant advantages thereof will be readily apparent by reference to the accompanying drawings, wherein:

FIG. 1a is a graph of voltage amplitude vs. time illustrating a substantially symmetric square wave signal for bone growth stimulation;

FIG. 1b is a compacted representation of FIG. 1a defining various terms utilized to describe the present invention;

FIG. 3 compares the energy transform efficiencies of various transducer coils;

FIG. 10 illustrates a sinusoidal pulse waveform which could be substituted for that of FIgure 1a; and FIG. 11 shows a ramp or triangular pulse waveform which could be substituted for that of FIG. 1a.

DETAILED DESCRIPTION OF THE PREFERRED EMBODIMENTS OF THE INVENTION

The present method and apparatus comprising this invention may be practiced in many different ways. It will be understood by those of ordinary skill in the art that the present discussion is with respect to an example of the present invention and should not be construed as a limitation on the material or methods described. For the purposes of this discussion, and the examples, the invention is described with respect to promoting osteogenesis or bone growth in the healing of bone fractures but it is understood that the application of the present invention is to healing all living tissues which include not only bone but also soft tissue.

The present invention is the application of an electromagnetic signal to the vicinity of the tissue area in which growth is to be stimulated. The electromagnetic signal has essentially a substantially symmetric waveform comprising a train of pulses having positive and negative amplitudes and a particular range of pulse widths, burst widths, peak amplitudes and frequencies. A significant benefit of this signal is that it consumes dramatically less energy than existant state of the art devices while still providing similar tissue healing effects. This reduction is due to the low pulse width (0.5 to 20 microseconds), and lower (50–200 mV) pulse amplitudes. The electromagnetic field created by the signal results in an associated electric field established by the fluctuating electromagnetic field within the tissue and this is proportional to dB/dt, the rate of change of the magnetic flux density (B) with respect to time (t). It is the combined amplitudes of the magnetic flux and the associated electric field within the tissue that promotes the healing. Since the power required to generate a signal is a function of the pulse width squared, the pulse needed to establish an effective treatment signal can be reduced by narrowing the pulse width which is an aspect of the tissue healing which has not previously been discovered.

Pulse width is the only parameter which, when reduced, maintains a constant power density, electric field and current density in the tissue while simultaneously reducing the required input power. Reducing any of the other signal parameters (amplitude, burst width, burst frequency and duty cycle) reduces power density in the tissue when one attempts to reduce the input power. It can be shown that the power density, electric field and current density in the tissue are independent of the pulse width for a constant coil voltage ($V_{sc}=K(dB/dt)$).

Figure 10:
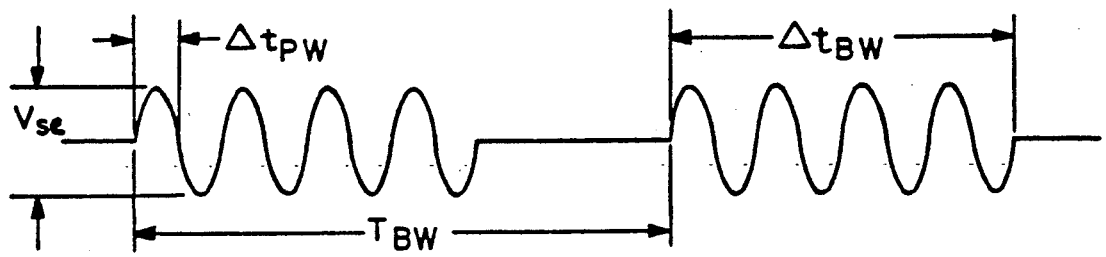
Figure 11:
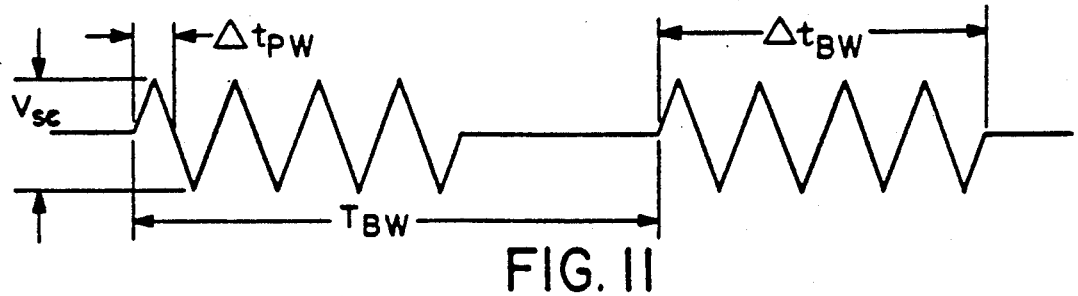

FIGS. 1a and 1b illustrate a square waveform of signal applied to stimulate tissue healing. However, alternatively, FIGS. 10 and 11 show sinusoidal and ramp or triangular waveforms which could also be utilized with advantageous results. The square wave in FIGS. 1a and 1b may be generated by any suitable signal generator which provides the time varying voltage to a suitable transducer located adjacent the desired area of tissue healing. It can be seen that the substantially symmetric square wave has a period $T_1$ (pulse burst length) including a series of individual pulses, each having a pulse width $\Delta T$ and an amplitude of $V_{sc}$. A single cycle is comprised of the pulse burst length $T_1$ and the quiet time $T_2$ and cycle time is defined as $T_1+T_2$. The signal comprising successive cycles is applied to the site of the injury for a time $T_3$ where $T_3$ is equal to $n(T_1+T_2)$ where n is the number of cycles applied. Then the signal is terminated for a time $T_4$. The ratio $T_3/(T_3+T_4)$ is the "duty cycle" of the signal.

The amplitude of the electromagnetic signal $V_{sc}$ is measured in millivolts by a search coil of 67 turns with a diameter of 5.8 mm with the axis of the search coil parallel to the flux density. At the fracture site the amplitude is a function of several parameters, including the type of transducer used to convert the electrical signal into an electromagnetic field and the geometry associated with the location of the injury. There are numerous transducers suitable for use with a symmetric signal having "bursted pulses", i.e., groups of pulses in a burst configuration. A typical transducer will have one or more conductors having a coil configuration with multiple turns of low resistance wire in combination with materials having high magnetic permeability. The application of FIG. 1a and FIG. 1b signals to such a coil yields a time-varying electromagnetic field for stimulation of tissue growth. Obviously, the number of turns, the selection of materials and the specific geometry of the coil can vary and may be optimized for varying tissue treatments.

A determination of the optimal transducer design requires a consideration of the power efficiencies of various transducers. One factor in determining the type of transducer to be used is the nature of the tissue injury sought to be treated. For example, to stimulate healing of a deeply buried bone such as the femur, a transducer capable of delivering energy through a considerable amount of soft tissue is desirable. A transducer requiring less power to maintain the same field strength (at the tissue area) can be employed for bone fractures nearer the skin, e.g., those of the tibia or clavicle.

Various preferred coil-type transducers have been found for treating deep bone fractures. The power needed for a coil-type transducer (Helmholtz paired coils, a simple coil, an oblique coil or a solenoid coil) is as follows:

$$P = (1 - n_{REC})(L/2f_c)^2(4 \times 10^6 V_{sc})^2 \Delta t_{PW} \Delta t_{BW} f_{BF} \quad \text{(Eq. 1)}$$

where $n_{REC}$ is the fractional energy recovery coefficient, L is the coil inductance, $f_c$ is coil sensitivity, $V_{sc}$ is search coil voltage appearing at the terminal of a 67-turn bobbin coil of diameter 5.8 mm (having an axis of the coil parallel to the flux density (B) vector) and $\Delta t_{PW} \Delta t_{BW}$ and $f_{BF}$ are pulse width, burst width and burst frequency, respectively. Clearly, a coil constant reflecting the power efficiency of the coil transducer can be represented as:

$$K_c = (L/f_c)^2 \quad \text{(Eq. 2)}$$

Figure 9:
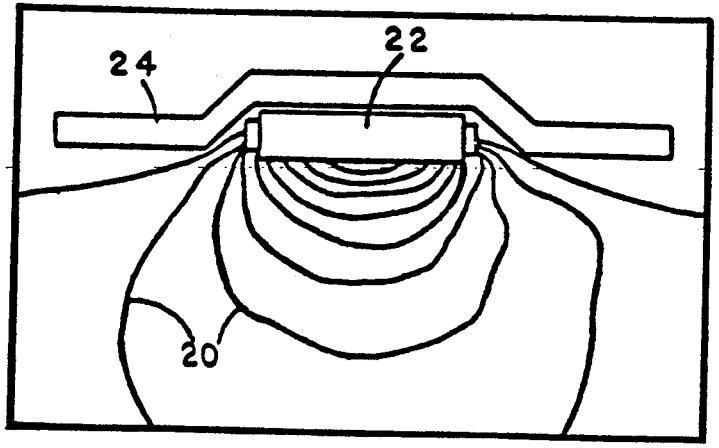
FIG. 9 is a schematic view similar to FIG. 7 showing the lines of flux of the magnetic field during operations.
Figure 6:
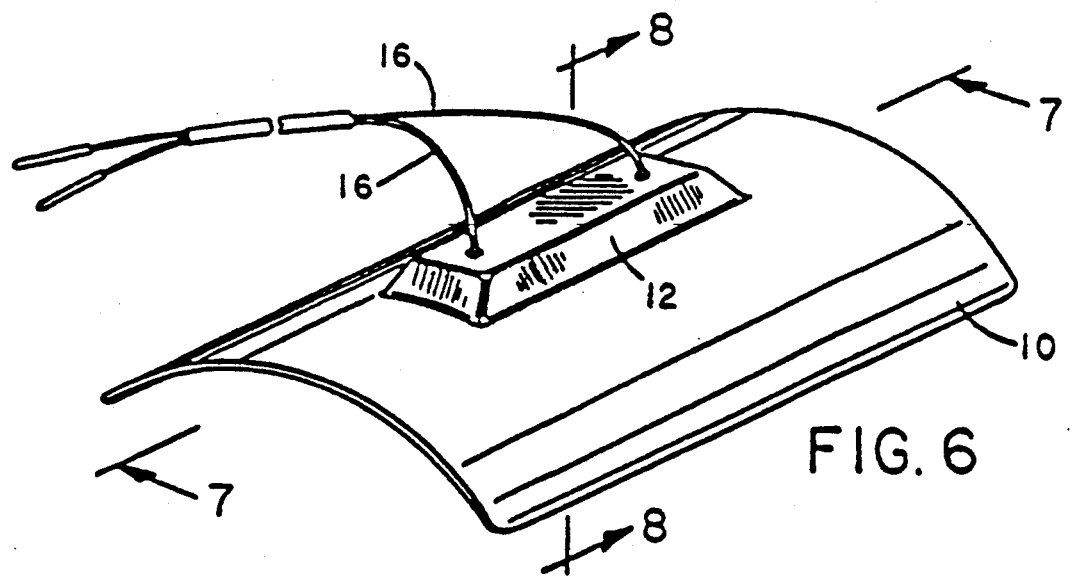
FIG. 6 is a perspective view of a conformal magnetic dipole transducer which can be used in a preferred embodiment of the present invention.
Figure 7:
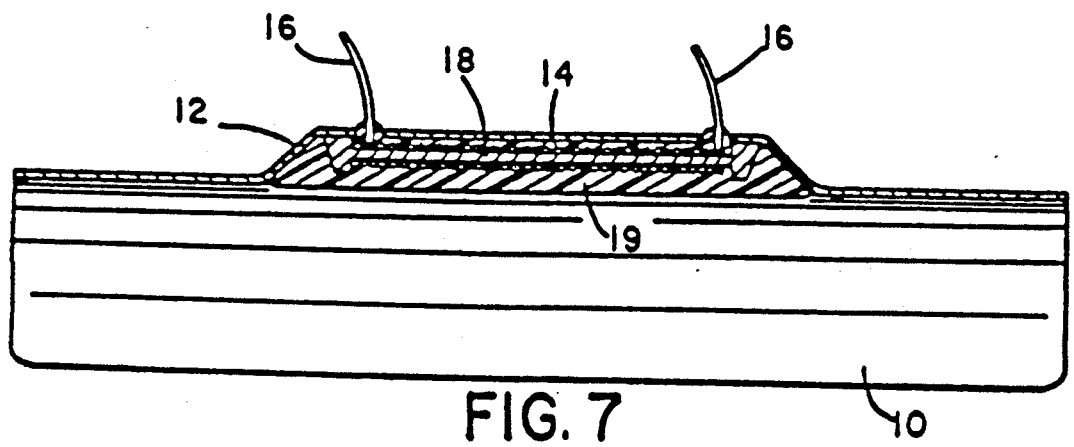
FIG. 7 is a side view, partially in section along section lines 7—7, of the dipole transducer of FIG. 6.
Figure 8:
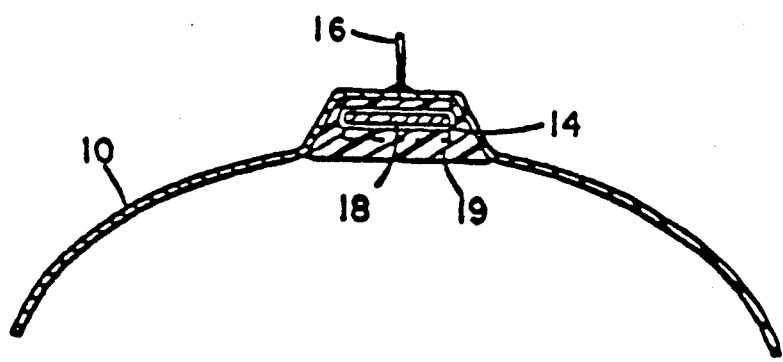
FIG. 8 is a sectional view along section lines 8—8 of the dipole transducer of FIG. 6.

A comparison of $K_c$ for several coil type transducers is shown in FIG. 3 which indicates that a solenoid type coil is the most energy efficient. Another transducer which is effective is the conformal magnetic dipole (CMD) which establishes shallow, focused fields on fracture or tissue parts such as the tibia, ulna, radius, clavicle, or scaphoid. In FIGS. 6–8, one example of a CMD is disclosed which includes a metal shield 10 having an uplifted region 12 for housing the transducer coil 14. Current is supplied through wires 16 and flows through coil 14 which is wound around a suitable support element 18. The coil is preferably potted in place in the raised area of the shield by suitable glue, resin or the like 19. FIG. 9 illustrates the lines of magnetic flux 20 of the field emitted from coil 22 with respect to metal shield 24 in a representational view of the conformal magnetic dipole disclosed in FIGS. 6–8.

The conformal magnetic dipole serves to capture or focus the flux emitting from the coil towards the fracture zone and is believed to result in a 20 to 40% power savings while at the same time reducing exposure of other body regions to extraneous magnetic fields.

Figure 4:
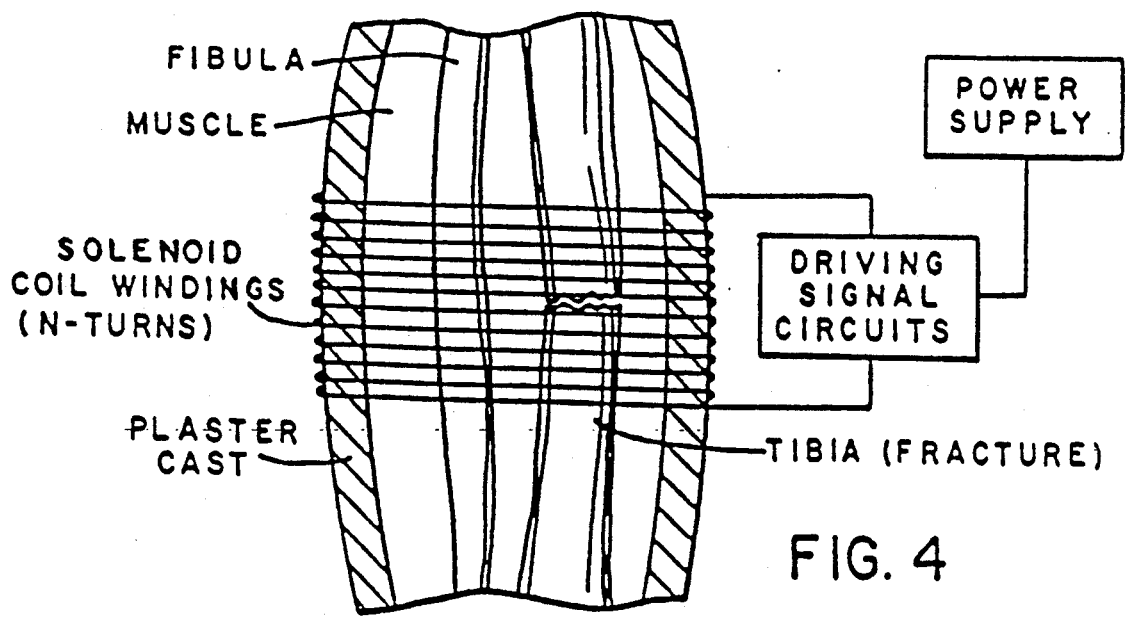
FIG. 4 is a side view, partially in section, of a patient's leg having a fractured tibia and illustrates the present invention in use to promote healing.
Figure 5:
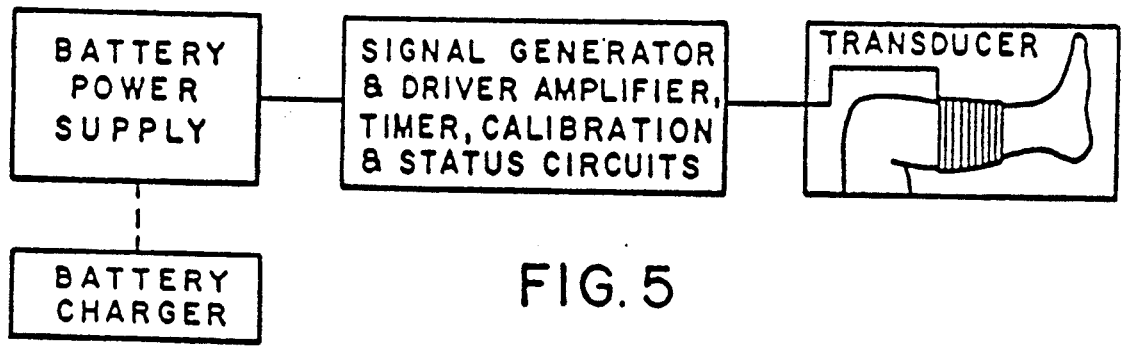
FIG. 5 is a schematic block diagram of one embodiment of the present invention.

While a conformal magnetic dipole has been shown successful, other coil transducers as noted above may also be employed. Because of the low power requirements, a battery powered electromagnetic therapy unit can be constructed for treating shallow or deep fractures. FIG. 5 provides a schematic block diagram for such a portable unit. FIG. 4 illustrates in more detail the applicability of a solenoid type coil to the healing of a tibia fracture and the incorporation of such a coil with a portable electromagnetic therapeutic device. The leg comprising muscle tissue, fibula and tibia is encased in a suitable plaster or fiber glass cast which has a solenoid coil wrapper therearound. The coil is connected to the driving signal circuit which is powered by the power supply as indicated. The signal generator and the power supply may be located a distance away from the coil, for example, on a user's belt. Alternatively, all components may be attached or integrated into the cast. Where long term use is required necessitating battery replacement for recharging (as by battery charger shown in FIG. 5) the waist belt mounting may be most convenient. However, for simple or small geometry fractures the time of application for maximum rate of healing stimulation may be relatively small without the requirement of changing batteries over the required stimulation period. In this instance it may be desirable to integrate the entire structure into the cast. It can be seen that unlike prior art high power consumption systems, the present invention can be truly portable and relatively unobtrusive, aiding in patient compliance with the therapy schedule.

With modern production methods, it is expected that the power source and signal generator circuitry will weigh less than one pound and be about the size of a compact pocket camera. The battery will provide voltages on the order to 6 to 40 volts and will have a battery volume on the order of 2 to 60 cubic cm. It is envisioned that the batteries, due to the energy efficiency of the invention, would not have to be replaced for at least several days and perhaps not for months. Table I below shows different calculated ranges of useable hours of a test device as a function of the different numbers of batteries, coils and signal pulse widths. For this example, the device had a solenoid-type transducer with a diameter of 12.7 cm, and L/d ratio of about 1 and a resistance of 0.63 ohm. Obviously variations upon these parameters will vary the size and quantity of batteries needed. The information in the table was derived using the equation:

$$I_B = I_{OH} + [(K_c V_{sc}^2 \Delta t_{PW}^2)(R_g + NR_t)/(V_S N^2) - \Delta t_{BW} f_{BF} - 0.002/V_S] \quad \text{(Eq. 3)}$$

where:
$I_B$ = Battery current
$I_{OH}$ = Overhead current
$K_c$ = Coil constant
$\Delta t_{PW}$ = Pulse width (5 sec.)
N = Turns coil
$V_S$ = Battery voltage
$R_g$ = Driver circuit output resistance
$R_t$ = Resistance/turn
$\Delta t_{BW}$ = Burst width (5 msec)
$f_{BW}$ = Burst frequency (15 Hz)
$V_{sc}$ = 200 mV
and where
$V_{sc}$ = 200 mv, $\Delta t_{PW}$ = 5 sec, $\Delta t_{BW}$ = 5 msec and $f_{BF}$ = 15 Hz.

TABLE I

| Battery type | $V_{Bmin}$ | N | $\Delta t_{PW}$ μs | $I_{BA}$ mA-hrs | Cap mA-hrs | Dus hrs. | Wt g |
|---|---|---|---|---|---|---|---|
| 12 - ⅔ AD NiCAD | 13.2 | 20 | 5 | 16.4 | 300 | 18.3 | 148 |
| 15 ⅔ AA NiCAD | 16.5 | 26 | 5 | 8.7 | 300 | 34.4 | 1858 |
| 3 × 9 V NiCAD | 23.1 | 37 | 5 | 3.7 | 100 | 27 | 138 |
| 2 × 9 V Alkaline | 12 | 19 | 5 | 21.6 | 450 | 21 | 92 |
| 3 × 9 V | 18 | 28 | 5 | 6.9 | 450 | 65 | 138 |
| P.P. Lithium (2) | 10 | 15 | 5 | 37.2 | 1300 | 35 | 68 |
| 6 ⅔ A Lithium | 15 | 23 | 5 | 11.4 | 916 | 80 | 81 |
| 2 "9 V" Zn Air | 13 | 20 | 5 | 17.1 | 700 | 41 | 60 |
| 9 ⅔ Lithium | 22.5 | 35 | 7 | 7.1 | 916 | 129 | |
| 15 ⅔ AA NiCAD | 16.5 | 26 | 7 | 16.6 | 300 | 18.1 | |
| 3 - "9 V" NiCAD | 23.1 | 37 | 7 | 6.65 | 100 | 15 | |
| 3 - "9 V" Akaline | 18 | 28 | 7 | 13 | 450 | 35 | |
| 2 - "9 V" Zn-Air | 13 | 20 | 7 | 33 | 700 | 21 | |
| 6 - 9 V Akaline | 36 | 57 | 7 | 2.4 | 450 | 188 | |
| 2 - 9 V Akaline | 12 | 19 | 3 | 8 | 450 | 56 | |
| 3 - 9 V Akaline | 18 | 28 | 3 | 2.9 | 450 | 157 | |
| 6 - ⅔ A Lithium | 15 | 23 | 3 | 4.5 | 916 | 204 | |
| 15 - ⅔ AA NiCAD | 16.5 | 26 | 3 | 3.5 | 300 | 86 | |
| 6 - ⅔ A Lithium | 15 | 23 | 10 | 44 | 916 | 21 | |
| 9 - ⅔ A Lithium | 27.5 | 36 | 10 | 13.9 | 916 | 66 | |
| 3 - PP Lithium | 15 | 23 | | 44 | 1300 | 30 | |

It also appears, in Equation 3 and in Table I, that N, the number of turns comprising the solenoid, is dependent upon the maximum applied voltage, transducer sensitivity and specified search voltage and can be optimized for the particular application.

The utility of the FIG. 1a and 1b signals was established using an animal model system, in this case a rabbit fibula system, such as described by Brighton et al, *J. Orthopaedic Res.*, 3,331, (1985). Rabbits undergo a midshaft transverse osteotomy of one fibula, after which a suitable transducer is placed around the fracture site and connected to a power supply. Both experimental and control animals were treated with the signal shown in FIGS. 1a and 1b. It was found that $\Delta t_{PW}$ could be within the range of 0.5–20 microseconds, although preferably 2 to 10 microseconds would be used with 5 microseconds being particularly effective. Current prior art devices operate in the range of 20–300 microseconds and some generate asymmetric signals.

Although the present invention is not bound to a particular theory of operation it is believed to have theoretical justification. How and why electromagnetic radiation stimulates bone growth repair is not completely understood, although it is believed necessary to require delivery of a signal to the injured site having defined time constants for burst width and burst frequency. To accomplish this it is necessary for the electromagnetic signal to be established in healthy tissue and reach the injured tissue site without being significantly attenuated by tissue. This would suggest that the time constant associated with the magnetic, electric, chemical and electro diffusion effects caused by the signal exhibit particular time constants. Table II below (from Grodzinsky) *Electric Fields, Forces, and Flows in Biological Tissue* (MIT, Lecture Handouts July 1983) and Ohashi et al., "The Electric Current Ratio of the Bone in the Rabbit Thigh For Capacitively Coupled Electric Field," Fifth Annual BRAGS (Boston, Mass.; October 13,-17, 1985), indicates that below 100 MHz the magnetic field completely penetrates through to the injured site. For electric "diffusion", penetration of the bone by the displacement current density remains low until after 1 MHz (the equivalent of 0.5 microseconds). Additionally, the viscous flow of interstitial fluids in the canaliculi can follow frequencies up to 1 MHz. In contrast, however, mechanical stress frequency responses attenuate after 500 Hz. Based on this brief analysis, it is apparent that signal current densities with pulse widths as low as 0.5 microseconds would very likely be established in the tissue, and thus would probably be responsible for therapeutically effective results.

Data was derived from a study in which animals were sacrificed at the mid phase of healing (i.e., after 14 days of treatment) and the mechanical stiffness of the healing callus of osteotomized bones from both treated and untreated animals was measured. The mechanical stiffness is essentially the slope of the load-deformation curve of the fractured and the intact fibula in the same animal (stiffness equals force per unit deflection). Variations in fibula strength for individual animals was controlled by dividing the stiffness of the fractured fibula by the stiffness of the contralateral intact fibula (the stiffness ratio). Flexure stiffnesses of animals in the experimental group were compared to those of control animals at various pulse widths and amplitudes. The fibula were mechanically tested for three-point bending stiffness in a CGS Lawrence testing apparatus as described by Brighton et al, referenced above. The maximum resistance to bending was also measured for the fibula. The results indicated that the strength, of the healed bone subjected to effective electromagnetic therapy, increased by as much as 50% for particular types of signals.

The above flexure stiffness findings were confirmed by radiologic and histologic data obtained on the 16th day of healing, which showed enhanced bone growth. Radiologic data was generated as follows: Anteroposterior and lateral roentgenograms were made of each fibula using fine grain industrial film (Kodak Type R). The degree of fracture healing was rated using the roentgenograms as follows: the fracture callus was examined in each of four equal quadrants for the presence of bone bridging across the fracture gap. If no calcified trabeculae bridged the fracture gap in any of the four locations, the rating was 0. The rating increased to 4 if trabeculae bridged the gap in all 4 locations. Differences in the roentgenographic rating between paired experimental and control fractures in each parametric group were evaluated for statistical significance using appropriate nonparametric statistical methods.

Histological data was generated as follows. The fibula were decalcified, embedded in paraffin, sectioned longitudinally at 6 micrometers and stained with hematoxylin and eosin. Sections from the center and one from each cortex were rated microscopically. The width of the fracture callus was divided into four equal parts (sectors) and a 12 point rating system was used. A

TABLE II

| PHYSICAL EFFECT | DEFINING EQUATION | $\tau$ TIME CONSTANT | $f_B = \frac{1}{T}$ EQUIVALENT BREAK FREQUENCY | EQUIV. $\Delta t_{PW}$ | PARAMETERS |
|---|---|---|---|---|---|
| MAGNETIC DIFFUSION | $\frac{\delta H}{\delta t} = \frac{1}{\mu \sigma} \nabla^2 H$ | $S^2 \mu \sigma$ | $\frac{2}{(25 \times 10^{-4}) \times 4\pi \times 10^{-7}} \approx 100$ MHz | 5 ns | $\mu$ = permeability<br>$\sigma$ = conductivity<br>H = field |
| ELECTRIC DIFFUSION | $\nabla \cdot \sigma E = \frac{\delta \rho}{\delta t}$ | $\frac{\epsilon}{\sigma}$ | $\frac{1}{10^{-6}} \approx 1$ MHz | 0.5 $\mu$s | $\epsilon$ = permitivity<br>$\mu$ = permeability |
| VISCOUS DIFFUSION | $\frac{dV}{dt} = \frac{n}{\rho} \nabla 2 V$ | $\frac{\rho R^2}{n}$ | $\frac{10^{-3}}{10^3 (10^{-6})^2} \approx 1$ MHz | 0.5 $\mu$s | n = viscosity<br>$\rho$ = density<br>R = channel radius (1 $\mu\pi$) |
| MECHANICAL | | $\frac{\delta^2}{mk}$ | $\frac{.5 \times 10^{+6} \times 10^{-15}}{10^3 (10^{-6})^2} \approx 500$ Hz | 2 ms | m = modulus of elasticity<br>k = hydraulic displacement coefficient | rating of 1 through 4 was given if only fibrous tissue bridged the gap. The rating was 1 if fibrous tissue either did not bridge the gap in any sector or did so in only one sector with the rating increasing to 4 if fibrous tissue bridged the gap in all sectors. A rating of 5 through 8 was given if cartilage bridged the gap in 1 through 4 sectors, respectively, without bone bridging. A rating of 9 through 12 was given if bone bridging occurred in 1 through 4 sectors, regardless of the presence of cartilage. Each of the three sections from each fibula was rated and the average used. Ratings between paired experimental and control fractures in each group were evaluated for statistical significance by appropriate non-parametric tests.

Table III below shows that there is a statistically significant increase in the stiffness ratio as a function of increased pulse width within the range of 2–7 microseconds. Additionally, within this range of pulse widths there is a significant increase in bone growth in the fractured area (shown by both histological and radiological data). Table IV shows that there is an increase in the stiffness ratio as a function of the increased signal amplitudes within the range of 10–75 mV, particularly at a search coil voltage ($V_{sc}$) of 50 mV. There is also a further increase at 75 mV which appears to correspond with significant enhanced bone growth based on the histological data. The 50 mV amplitude appears to have enhanced bone growth confirmed by the radiological data.

over a range of 0.5–200 microseconds, only a range of 0.5–20 microseconds can be supported by the lower power available in a truly portable system. It was observed that the amplitude of the signal could vary from 25–200 millivolts with a preferred amplitude in the range of 50–100 millivolts. Obviously a number of variations on the above signal could be utilized and positive therapeutic results could be expected. Lower values of $T_1$ and higher values of $T_2$ would be applicable. It is possible that $T_1$ as low as one millisecond and $T_2$ as high as several hundred milliseconds could be employed. Further, the duty cycle does not necessarily have to be limited and values of $T_3$ in the range of 1 to several hundred seconds with corresponding $T_4$ values an order of magnitude higher than those attempted may be useable.

Additional data derived from experiments in which electromagnetic therapy was utilized for a 14 day period details changes caused by variations in $V_{sc}$, $\Delta t_{PW}$ and duty cycle. Following treatment both control and experimental animals were sacrificed and the fractured fibula excised. The previously discussed 3 point bending stiffness test as well as a maximum resistance to bending was measured for all fibulae. The stiffness ratios of electromagnetically stimulated rabbits was compared to the non-electromagnetically stimulated rabbits Tables V and VI below illustrate the results of the tests with examples of stiffness ratio measurements over a range of pulse widths given in microseconds at 100 mV (Table

TABLE III

| | | UNSTIMULATED (CONTROL) GROUP | STIMULATED (EXPERIMENTAL) GROUPS | | | | | | |
|---|---|---|---|---|---|---|---|---|---|
| | | | 0.5 μs | 1 μs | 2 μs | 3 μs | 4 μs | 5 μs | 6 μs |
| MECHANICAL DATA: STIFFNESS RATIOS | MEAN | 0.201 | 0.190 | 0.131 | 0.256 | 0.210 | 0.211 | 0.247 | 0.313* |
| | STANDARD DEVIATION | 0.112 | 0.101 | 0.074 | 0.170 | 0.124 | 0.107 | 0.172 | 0.128 |
| | NUMBER | 103 | 8 | 8 | 14 | 25 | 8 | 56 | 15 |
| HISTOLOGICAL DATA: SCORES | MEAN | 9.9 | 8.2 | 9.1 | 8.4 | 10.7 | 10.3 | 9.9 | 11.6 |
| | MEAN RANK | 109.5 | 47.9 | 77.6 | 63.5 | 148.4 | 126.2 | 112.4 | 168.0 |
| | N | 102 | 8 | 8 | 14 | 25 | 8 | 47 | 15 |
| RADIOLOGICAL DATA: SCORES | MEAN | 5.8 | 5.1 | 5.1 | 5.4 | 6.1 | 6.3 | 6.2 | 7.1 |
| | MEAN RANK | 112.2 | 81.8 | 78.4 | 104.2 | 123.9 | 125.6 | 130.0 | 162.9* |
| | N | 104 | 8 | 8 | 14 | 25 | 8 | 54 | 15 |

TABLE IV

| | | UNSTIMULATED (CONTROL) GROUP | STIMULATED (EXPERIMENTAL) GROUPS | | | |
|---|---|---|---|---|---|---|
| | | | 10 mV | 25 mV | 50 mV | 75 mV |
| MECHANICAL DATA: STIFFNESS RATIOS | MEAN | 0.201 | 0.189 | 0.159 | 0.331 | 0.295 |
| | STANDARD DEVIATION | 0.112 | 0.116 | 0.070 | 0.136 | 0.161 |
| | NUMBER | 103 | 11 | 11 | 18 | 21 |
| HISTOLOGICAL DATA: SCORES | MEAN | 9.9 | 9.8 | 9.4 | 10.0 | 10.8 |
| | MEAN RANK | 109.5 | 111.4 | 95.3 | 118.8 | 149.7 |
| | N | 102 | 11 | 9 | 17 | 21 |
| RADIOLOGICAL DATA: SCORES | MEAN | 5.8 | 5.2 | 5.5 | 6.8 | 6.1 |
| | MEAN RANK | 115.2 | 92.5 | 99.1 | 153.0 | 130.3 |
| | N | 104 | 11 | 11 | 18 | 21 |

With respect to the square wave signal shown in FIGS. 1a and 1b, data indicated that the most effective parameters associated with the signal comprised:

$T_1 = 1$–10 milliseconds
$T_2 = 60$–65 milliseconds
$T_3 = 12$ hours and 24 hours
$T_4$ 12 hours and 0 hours While data illustrates that the pulse width $\Delta t_{PW}$ with a square wave was effective (for therapeutic purposes)

V) and search coil voltage ($V_{sc}$) amplitudes in millivolts (Table VI). In both tables $f_{BF}$ - 15 Hz and $T_1$ - 5 msec. In Table V, $V_{sc} = 100$ mV and $\Delta t_{PW}$ varied from 2–10 microseconds. In Table VI, $\Delta t_{PW} = 5$ microseconds and $V_{sc}$ varied from 10–200 mV. In both tables, the average of the stiffness ratio is indicated by $<x>$ or x, the standard deviation of the test data by SD or $\sigma$ and the number of samples per test by N. The search coil has the characteristics previously discussed, i.e., 67 turns and a diameter of 5.8 mm.

TABLE V

| EXPERIMENT | CONTROL | 2 μs | 3 μs | 4 μs | 5 μs | 7 μs | 10 μs |
|---|---|---|---|---|---|---|---|
| 9 May | $<X> = 1.20$<br>SD = 0.78<br>N = 6 | | | | | | $<X> = .366$<br>SD = .194<br>N = 9 |
| 11 June July | $<X> = .236$<br>SD = .147<br>N = 7 | | | | $<X> = .312$<br>SD = .175<br>N = 18 | | |
| 16 Oct.-Nov. | $<X> = .244$<br>SD = .114<br>N = 4 | | | | $<X> = .302$<br>SD = .166<br>N = 5 | | |
| 18 Nov.-Dec. | $<X> = .207$<br>SD = .009<br>N = 2 | $<X> = .225$<br>SD = .097<br>N = 6 | | | $<X> = .216$<br>SD = .156<br>N = 6 | | |
| 19 Jan. | $<X> = .156$<br>SD = .029<br>N = 5 | $<X> = .265$<br>SD = .204<br>N = 9 | | $<X> = .156$<br>SD = .029<br>N = 5 | | | |
| 22 Feb. | $<X> = .156$<br>SD = .030<br>N = 6 | | | | | $<X> = .301$<br>SD = .043<br>N = 7 | |

TABLE VI

| EXPERIMENT | CONTROL | 10 mV | 25 mV | 50 mV | 75 mV | 100 mV | 125 mV | 200 mV |
|---|---|---|---|---|---|---|---|---|
| 9 May | $\bar{x} = .120$<br>$\sigma = .078$<br>N = 6 | | | | | | | $\bar{x} = .266$<br>$\sigma = .194$<br>N = 16 |
| 10 June | $\bar{x} = .128$<br>$\sigma = .044$<br>N = 6 | | | | | | | $\bar{x} = .142$<br>$\sigma = .086$<br>N = 9 |
| 11 June–July | $\bar{x} = .236$<br>$\sigma = .147$<br>N = 7 | | | | | $\bar{x} = .312$<br>$\sigma = .175$<br>N = 18 | | |
| 12.5 July–August | $\bar{x} = .201$<br>$\sigma = .097$<br>N = 3 | | | $\bar{x} = .464$<br>$\sigma = .074$<br>N = 7 | | | | |
| 13.5 August | $\bar{x} = .224$<br>$\sigma =$<br>N = 1 | | | $\bar{x} = .214$<br>$\sigma = .079$<br>N = 5 | | | | |
| 14 September | $\bar{x} = .226$<br>$\sigma = .107$<br>N = 5 | $\bar{x} = .189$<br>$\sigma = .116$<br>N = 11 | $\bar{x} = .113$<br>$\sigma = .072$<br>N = 3 | | | | | |
| 15 September–October | $\bar{x} = .167$<br>$\sigma = .076$<br>N = 4 | | $\bar{x} = .177$<br>$\sigma = .066$<br>N = 8 | $\bar{x} = .275$<br>$\sigma = .098$<br>N = 6 | $\bar{x} = .327$<br>$\sigma = .148$<br>N = 6 | | | |
| 15.5 October | $\bar{x} = .288$<br>$\sigma = .104$<br>N = 2 | | | | | $\bar{x} = .272$<br>$\sigma = .201$<br>N = 8 | | |
| 16 October–November | $\bar{x} = .244$<br>$\sigma = .114$<br>N = 4 | | | | | $\bar{x} = .295$<br>$\sigma = .139$<br>N = 7 | $\bar{x} = .302$<br>$\sigma = .166$<br>N = 5 | $\bar{x} = .359$<br>$\sigma = .237$<br>N = 8 |

The data in the above Tables can be more clearly understood if the definitions of stiffness ratio are remembered. Stiffness measures the resistance of an object to bending under a given load, the object in this case being bone and a higher value means a more rigid object. Because different animals may have different bone stiffnesses, the stiffness ratio compares the stiffness of an animal's intact fibula with the stiffness of the fibula of the same animal which has been broken and subsequently healed under the experimental conditions. Therefore, the higher the stiffness ratio, the more broken bone has healed and the more closely it approaches the stiffness of the intact bone.

Figure 2:
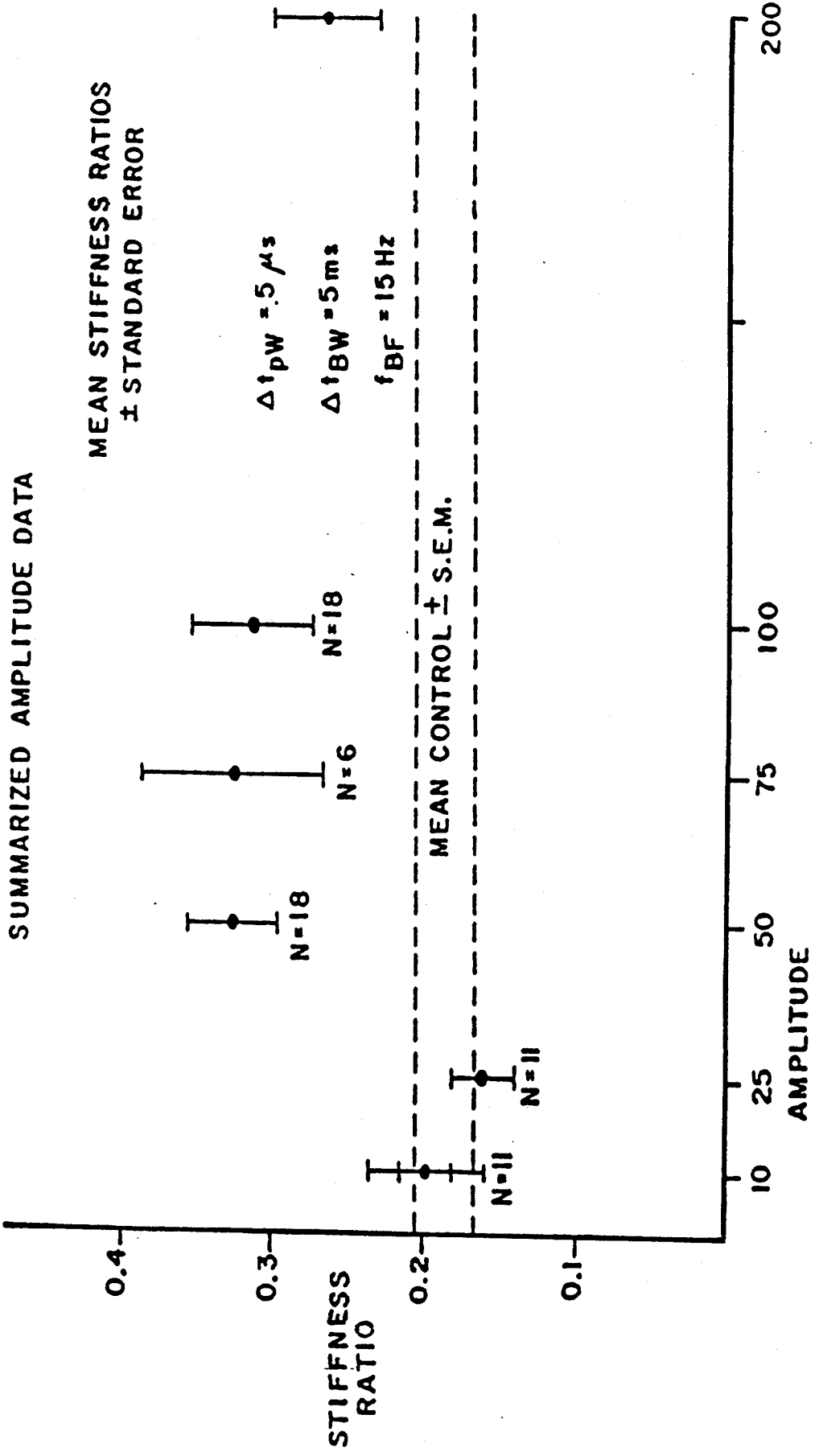
FIG. 2 is a graph of fracture stiffness ratio vs. effective signal amplitude for the present invention with a pulse width of 5 microseconds, where the period of pulse bursts is equal to 5 milliseconds and the burst frequency is equal to 15 Hz.

It will be seen that particularly advantageous results were obtained with $V_{sc} = 50$ to 200 mV, tpw is 5 microseconds, the burst frequency $f_{BF}$ is 15 Hz, and $T_1$ is 5 msec. Table V and FIG. 2 illustrates the effectiveness of the electromagnetic therapy. It will be appreciated that the experimental data indicative of the utility of the invention was obtained utilizing rabbits. However, rabbit bone growth is a well known model of human bone growth and it is expected that the parameters utilized to optimize bone growth in rabbits will be similarly applicable to larger animals and to humans. While this data was based on fresh fractures, it is believed clear in view of the present application that this invention will be capable of stimulating healing among various types of damaged tissues including bone fractures that do not readily heal in the absence of treatment, such as delayed unions, nonunions and failed fusions. In view of the above disclosures, it is submitted that there will be many variations and modifications of the present invention which will be obvious to those of ordinary skill in the art. Therefore, although the foregoing invention has been described with respect to a particular example and preferred embodiments, the invention is not so limited and indeed is limited only in accordance with the appended claims.

We claim:

1. A non-invasive electromagnetic therapeutic method to promote healing of tissue, said method comprising the steps of:

converting electrical potential into an electrical signal, said electrical signal comprising a series of substantially symmetric voltage cycles, each of said voltage cycles comprising a train of bursted pulses, each pulse having an average pulse width in the range of from 0.5 to 20 microseconds; and transducing said voltage cycles into an electromagnetic field in the vicinity of said tissue.

2. A method according to claim 1, wherein each of said cycles comprises first and second time periods, said first time period defined as a time period during which said signal comprises said train of pulses and said second time period being defined as a time period during which said signal is quiescent.

3. A method according to claim 1, wherein said electrical signal is a symmetric square wave.

4. A method according to claim 1, wherein said electrical signal is a symmetric sine wave.

5. A method according to claim 1, wherein said electrical signal is a symmetric triangular wave.

6. A method according to claim wherein said electrical signal is a symmetric rectangular wave.

7. A method according to claim 1, wherein said average pulse width is within the range of from 2 to 10 microseconds.

8. A method according to claim 1, wherein pulses in said train have an average amplitude in the range of from 25 to 200 millivolts.

9. A method according to claim 5, wherein pulses in said train have an average amplitude in the range of from 50 to 100 millivolts.

10. A method according to claim 2, wherein said first time period is in the range of from 1 to 10 milliseconds and said second time period is in the range of from 60 to 65 milliseconds.

11. A non-invasive, portable electromagnetic therapeutic method to promote healing of tissue, said method comprising the steps of:

converting electrical potential into an electrical signal, said electrical signal comprising a series of substantially symmetric voltage cycles, each of said voltage cycles comprising a train of bursted pulses, each pulse having an average pulse width in the range of from 0.5 to 20 microseconds; and transducing said voltage cycles into an electromagnetic field in the vicinity of said tissue.

12. A method according to claim 11, wherein each of said cycles comprises first and second time periods, said first time period defined as a time period during which said signal comprises said train of pulses and said second time period being defined as a time period during which said signal is quiescent.

13. A method according to claim 12, wherein said first time period is in the range of from 1 to 10 milliseconds and said second time period is in the range of from 60 to 65 milliseconds.

14. A method according to claim 11, wherein said electrical signal is a symmetric square wave.

15. A method according to claim 11, wherein said electrical signal is a symmetric sine wave.

16. A method according to claim 11, wherein said electrical signal is a symmetric triangular wave.

17. A method according to claim wherein said electrical signal is a symmetric rectangular wave.

18. A method according to claim 11, wherein said average pulse width is within the range of from 2 to 10 microseconds.

19. A method according to claim 11, wherein pulses in said train have an average amplitude in the range of from 25 to 200 millivolts.

20. A method according to claim 19, wherein pulses in said train have an average amplitude in the range of from 50 to 100 millivolts.

21. A non-invasive, portable electrotherapeutic method to promote healing of tissue or bone comprising the steps of:

connecting an electrical potential storage device to a means for converting electrical potential from said device into an electrical signal, said electrical signal comprising a series of substantially symmetric voltage cycles, said voltage cycles comprising a train of bursted pulses each having a pulse width in the range of about 0.5–20 microseconds;

connecting said means for converting said electrical power to a transducer means for transducing said voltage cycles into an electromagnetic field; and positioning said transducer means adjacent to said tissue or bone for a time sufficient for said electromagnetic field to stimulate healing of said tissue or bone.

22. A method as in claim 21 wherein each of said cycles comprises a first and a second time period, said first time period being a time period during which said signal comprises said train of pulses, and said second time period being a time period during which said signal is quiescent.

23. A method as in claim 22 wherein said first time period is on the order of 1–10 milliseconds and said second time period is on the order of 60–65 milliseconds.

24. A method as in claim 21 wherein said signal is at least one of a symmetric square, sine, triangular and rectangular wave.

25. A method as in claim 24 wherein said signal is a symmetric square wave.

26. A method as in claim 21 wherein said signal is applied adjacent said tissue or bone during an on time period and said application is terminated during an off time period, wherein said on time period continues for the number of voltage cycles of said electric signal.

27. A method as in claim 21 wherein said pulse width is on the order of 2–10 microseconds.

28. A method as in claim 21 wherein each pulse in said train has an amplitude in the range of 25–200 millivolts.

29. A method as in claim 28 wherein each pulse in said train has an amplitude in the range of 50–100 millivolts.

30. A non-invasive electrotherapeutic method for healing a nonunion bone fracture in a patient comprising:

producing by means of a signal generating device an electrical signal comprising a series of substantially amplitude-symmetric cycles, each of said cycles comprising a train of bursted voltage pulses having a pulse width t in the range of about 1–200 microseconds and continuing for a time period $T_1$ followed by a period $T_2$ during which no pulses are present;

transducing the voltage pulses of said cycles by means of a transducer into an electromagnetic field;

applying said electromagnetic field to the point of said fracture by positioning said transducer in contact with the body of said patient at a point proximate to the location in said patient's body of said fracture, said application of said field being continued for a time effective to stimulate healing of said fracture.

31. A method as in claim 30 wherein said train of voltage pulses forms a symmetric wave having at least one of a square, rectangular, triangular and sinusoidal shape.

32. A method as in claim 31 wherein said pulse train in said cycle has the form of a symmetric sinusoidal wave.

33. A method as in claim 31 wherein said pulse train in said cycle has the form of a symmetric rectangular wave.

34. A method as in claim 31 wherein said pulse train in said cycle has the form of a symmetric square wave.

35. A method as in claim 31 wherein said pulse train in said cycle has the form of a symmetric triangular wave.

36. A method as in claim 30 wherein said pulse width t is in the range of 1-20 microseconds.

37. A method as in claim 36 wherein said pulse width t is in the range of 3-7 microseconds.

38. A method as in claim 30 wherein $T_1$ is in the range of 1-5 milliseconds and $T_2$ is in the range of about sixty to several hundred milliseconds.

39. A method as in claim 38 wherein $T_1$ is approximately 5 milliseconds and $T_2$ is approximately 62 milliseconds.

40. A method as in claim 30 wherein said time periods $T_1$ and $T_2$ added together comprise a duty cycle $T_3$ during which said cycle continues, and said duty cycle is separated from the next adjacent duty cycle by an off-duty time period $T_4$.

41. A method as in claim 40 wherein $T_3$ is in the range of 12-24 hours and $T_4$ is from 10 seconds to 12 hours.

42. A method as in claim 30 wherein each of said pulses has an amplitude in the range of 50-200 millivolts.

43. A method as in claim 42 wherein said amplitude is in the range of 50-100 millivolts.

44. A method as in claim 43 wherein said fracture is of a bone of the arm or leg, and said transducer is positioned in contact with said arm or leg.

45. A method as in claim 44 wherein said fracture is a fracture deep within said patient's leg and said electromagnetic field is applied to said fracture by penetration through a substantial depth of soft tissue.

46. An apparatus for electromagnetic therapy to promote healing of tissue, said apparatus comprising:
   means for converting an electrical potential into a series of substantially symmetric voltage cycles, each of said voltage cycles comprising a train of bursted pulses, each of said pulses having an average pulse width of from 0.5 to 20 microseconds; and
   transducer means for transducing said voltage cycles into an electromagnetic field in the region of said tissue.

47. An apparatus according to claim 46, further including portable means for providing said electric potential.

48. An apparatus according to claim 47, wherein said portable means for providing said electrical potential comprises a battery.

49. An apparatus according to claim 46, wherein said tissue comprises damaged bone tissue.

50. An apparatus according to claim 49, wherein said transducer means is combined with a cast means for maintaining the structural integrity of said damaged bone tissue.

51. An apparatus according to claim 46, wherein said means for converting is a portable structure.

52. An apparatus according to claim 46, wherein said voltage cycles have a burst frequency within the range of from 5 to 25 Hz and a burst width within the range of from 1 to 10 milliseconds.

53. An apparatus according to claim 46, wherein said transducer means comprises a coil of wire.

54. An apparatus according to claim 46, wherein said means for converting includes means for providing a voltage cycle having a peak to peak amplitude in the range of from 25 to 200 millivolts.

55. An apparatus according to claim 46, wherein said bursted pulses comprises a rectangular wave.

56. A portable apparatus for electromagnetically stimulating bone growth, said apparatus comprising:
   an electrical potential source;
   means, connected to said source, for converting said electric potential to a series of substantially symmetric voltage cycles, each of said voltage cycles comprising a train of bursted pulses, each pulse having an average pulse width of from 2 to 10 microseconds and an average peak to peak amplitude of from 50 to 150 millivolts; and
   transducer means, in combination with a cast positioned about said desired region of bone growth, for transducing said voltage cycles into an electromagnetic field extending into said desired region of bone growth.

57. An apparatus according to claim 56, wherein said electrical potential source comprises a battery.

58. An apparatus according to claim 57, wherein said transducer means comprises a coil.

59. A portable apparatus for electromagnetic therapy to promote healing of bone, said apparatus comprising:
   means for converting an electrical potential into a series of substantially symmetric voltage cycles, each of said voltage cycles comprising a train of bursted pulses, each of said pulses having an average pulse width of from 0.5 to 20 microseconds; and
   transducer means for transducing said voltage cycles into an electromagnetic field in the region of the bone to be healed.

60. An apparatus according to claim 59, further including portable means for providing said electric potential.

61. An apparatus according to claim 59, wherein said transducer means is combined with a cast means for maintaining the structural integrity of the bone to be healed.

62. An apparatus according to claim 60, wherein said potable means for providing said electrical potential comprises a battery.

63. An apparatus according to claim 59, wherein said voltage cycles have a burst frequency within the range of from 5 to 25 Hz and a burst width within the range of from 1 to 10 milliseconds.

64. An apparatus according to claim 59, wherein said transducer means comprises a coil of wire.

65. An apparatus according to claim 59, wherein said means for converting includes means for providing a voltage cycle having a peak to peak amplitude in the range of from 25 to 200 millivolts.

66. A portable apparatus for electrotherapy of damaged bone comprising:

a source of electrical potential connected to a means for converting said electric potential into a series of substantially symmetric voltage cycles, said voltage cycles comprising a train of bursted pulses each having a pulse width of 0.5–20 microseconds, and a transducer means in association with a cast adapted to be positioned about said damaged bone for transducing said voltage cycles into an electromagnetic field into said damage bone.

67. An apparatus as in claim 66 wherein said source of electrical potential is a battery having a voltage of about 6–40 volts and a volume of about 2–6 cubic centimeters.

68. An apparatus as in claim 66 wherein said voltage cycle comprises a symmetric electric signal having a frequency of about 5–25 Hz and a burst width of about 1–10 milliseconds.

69. An apparatus as in claim 68 wherein said signal generated is at least one of a square, sine, triangular and rectangular wave.

70. An apparatus as in claim 69 wherein said signal generated is a square wave.

71. An apparatus as in claim 66 wherein said transducer means is a coil transducer selected from the group consisting of a conformal solenoid, conformal magnetic dipole, oblique coil and simple coil.

72. An apparatus as in claim 71 wherein said transducer means is a conformal solenoid.

73. An apparatus as in claim 71 wherein said transducer means is a conformal magnetic dipole.

74. An apparatus as in claim 66 further comprising a voltage cycle having a peak to peak amplitude in the range of 25–200 millivolts.

75. An apparatus as in claim 66 wherein said association of said transducer means with said cast comprises integrating said transducer means into said cast causing it to be closely proximal to said damaged tissue or bone.

76. A portable apparatus for stimulating tissue or bone healing comprising an electric potential source connected to a means for converting said potential to a series of substantially symmetric voltage cycles, said voltage cycles comprising a train of bursted pulses each having a pulse width of about 2–10 microseconds and a peak to peak amplitude of about 50–150 millivolts, and a transducer means in association with a cast adapted to be positioned about damaged tissue or bone for transducing said voltage cycles into an electromagnetic field into said damaged tissue or bone to stimulate healing.

77. An apparatus as in claim 76 wherein said source of potential is a 6–40 volt battery having a volume of about 2–60 cubic centimeters.

78. An apparatus as described in claim 76 wherein said transducer means is a coil transducer selected from the group consisting of a conformal solenoid, conformal magnetic dipole, oblique coil and simple coil.

79. An apparatus as described in claim 78 wherein said transducer means is a conformal solenoid.

80. An apparatus as described in claim 78 wherein said transducer means is a conformal magnetic dipole.

81. An apparatus as described in claim 76 wherein said association of said transducer means with said cast comprises integrating said transducer means into said cast causing it to be in close proximity to said damaged tissue or bone.

* * * * *

UNITED STATES PATENT AND TRADEMARK OFFICE
CERTIFICATE OF CORRECTION

PATENT NO. : 5,014,699
DATED : MAY 7, 1991
INVENTOR(S) : SOLOMON R. POLLACK ET AL.

It is certified that error appears in the above-identified patent and that said Letters Patent is hereby corrected as shown below:

Column 9, lines 47-68:

Correct TABLE II, 1st column as follows:

| PHYSICAL EFFECT | DEFINING EQUATION |
|---|---|
| MAGNETIC DIFFUSION | $\dfrac{\delta \bar{H}}{\delta t} = \dfrac{1}{\mu \sigma} \nabla^2 H$ |
| ELECTRIC DIFFUSION | $\nabla \cdot \sigma \bar{E} = \dfrac{\delta \rho}{\delta t}$ |
| VISCOUS DIFFUSION | $\dfrac{d\bar{V}}{dt} = \dfrac{n}{\rho} \nabla 2 \bar{V}$ |

Signed and Sealed this

Third Day of November, 1992

*Attest:*

DOUGLAS B. COMER

*Attesting Officer*     *Acting Commissioner of Patents and Trademarks*